United States Patent [19]

Siebert et al.

[11] Patent Number: 4,888,296

[45] Date of Patent: Dec. 19, 1989

[54] MONOCLONAL ANTIBODIES RECOGNIZING L-THYROXINE

[75] Inventors: Gary R. Siebert, Raleigh, N.C.; Jean Armstrong, Bogota, N.J.

[73] Assignee: Becton, Dickinson and Company, Franklin Lakes, N.J.

[21] Appl. No.: 899,115

[22] Filed: Aug. 22, 1986

Related U.S. Application Data

[62] Division of Ser. No. 631,048, Jul. 16, 1984, Pat. No. 4,636,478.

[51] Int. Cl.[4] .................. G01N 33/53; C12N 5/00; A61K 39/395

[52] U.S. Cl. .................. 436/500; 435/240.26; 435/240.27; 530/387; 424/85.8

[58] Field of Search .................. 435/240.26, 240.27; 530/387; 436/500; 424/85.8

*Primary Examiner*—Margaret Moskowitz
*Assistant Examiner*—Abdel A. Mohamed
*Attorney, Agent, or Firm*—Richard E. Brown

[57] ABSTRACT

Monoclonal antibodies specific for thyroxine ($T_4$) are produced by two new and separate hybridoma cell lines. Combinations of the monoclonal antibodies from the two cell lines are used in an immunoassay for $T_4$ of high accuracy over the range of $T_4$ concentrations encountered in serum samples.

8 Claims, No Drawings

MONOCLONAL ANTIBODIES RECOGNIZING L-THYROXINE

This is a division of Ser. No. 631,048, filed 7/16/84, now U.S. Pat. No. 4,636,478.

1. Field of the Invention

The present invention relates generally to an assay for a ligand. More particularly, the invention relates to the use of monoclonal antibodies in an assay for L-thyroxine.

2. Description of the Prior Art

Immunologically based diagnostic assays have traditionally used mixtures of antibodies, referred to herein as polyclonal antibodies. Polyclonal antibodies are elaborated in animals by B-lymphocytes in response to the challenge of an antigen, such as a toxin, bacteria, virus or a foreign cell, which invades or is introduced into the animal. Antigens have one or more surface markers, or determinants, which are recognized as foreign by the lymphocytes.

A given lymphocyte recognizes only one determinant of the antigen, and elaborates only a single antibody. The antibody which it elaborates is specific only for an antigen having that determinant. However, most antigens have many determinants, and other lymphocytes will produce antibodies against each of these determinants. In addition, since the number of antigens is unlimited, the individual will likely possess antibodies from previous antigenic challenges. As a result, the individual will possess in its serum a large pool of different, or polyclonal, antibodies.

Known antisera are based on polyclonal antibodies. Even after many isolation and purification steps, polyclonal antibodies are still heterogeneous. Such heterogeneity may limit the specificity of the antiserum and thereby reduce its effectiveness as an immunological reagent, such as a diagnostic reagent.

Monoclonal antibodies are homogeneous and thereby eliminate many of the problems associated with conventional antisera based on polyclonal antibodies. In the preparation of monoclonal antibodies, a mouse is typically injected with the antigen (the immunization step), and, after a period of time, antibody-making lymphocytes are isolated, usually from the spleen. The lymphocytes are fused with myeloma cells to provide fused cells, referred to as hybridomas. The hybridomas are separated from unfused lymphocytes and myeloma cells. Specific hybridomas are isolated and tested to establish that the isolated hybridoma does indeed produce antibody specific for the antigen used in the immunization step. The hybridoma so produced combines the ability of the parent lymphyocyte cell to produce a specific single antibody with the ability of its parent myeloma cell to continually grow and divide, either in vitro as a cell culture or in vivo as a tumor after injection into the peritoneal cavity of an animal.

Monoclonal antibodies possess several advantages over polyclonal antibodies. They are produced by a single hybridoma cell line and are thus absolutely homogeneous. The antigen used in the immunization step does not have to be pure. Monoclonal antibodies are produced by a hybridoma which can grow indefinitely in cell culture or in an animal. Monoclonal antibodies can be obtained in almost unlimited quantity, and the supply is not limited to the lifetime of a producing animal.

Haptens are low molecular weight non-protein substances which are capable of interacting with an antibody, but which are not immunogenic themselves. When haptens are coupled with a protein carrier, they can be made to elicit an immune response by a lymphocyte to produce an antibody. The antibodies thus formed do recognize and react with the hapten in the absence of the protein carrier. Exemplary of haptens are steroids, prostaglandins, thyroxine and various drugs.

Until relatively recently, sensitive and specific methods for measuring the concentration of haptens in serum were not available. In recent years, various immunoassay procedures have been developed. The technique of competitive radioimmunoassay is described in general by the following equation wherein the asterisk represents a radioactive label:

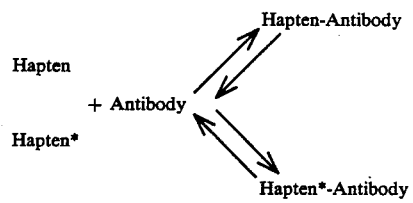

In this procedure, the unlabeled hapten competes with labeled hapten for a limited number of available antibody binding sites, thereby reducing the amount of labeled hapten bound to antibody. The level of radioactivity bound is, therefore, inversely related to the concentration of hapten in the patient sample or standard. After an adequate incubation period, the bound and free fractions are separated and the radioactivity is quantitated.

The amino acid 3, 5,3',5'- tetraiodo-L-thyronine is commonly called thyroxine and is often referred to as $T_4$. The designation $T_4$ is understood to mean the L isomer. It is a hormone having as its principal function a stimulating effect on metabolism.

$T_4$ is the predominant iodothyronine secreted from the thyroid, and the measurement of serum $T_4$ concentration has become the test commonly employed as an initial procedure in the diagnosis of states of altered thyroid function, such as hyperthyroidism or hypothyroidism. In addition, it is well known that several conditions other than thyroid disease may cause abnormal serum levels of $T_4$. Among these are pregnancy, estrogenic or androgenic steroids, oral contraceptives, hydantoins and salicylates, stress, hyper- and hypoproteinemia, and conditions (hereditary or acquired) which cause alterations in serum levels of thyroid binding globulin (TBG) the major serum $T_4$ transport system.

Early $T_4$ determinations were indirect measurements of the concentration of protein-bound or butanol-extractable iodine in serum. Later, competitive protein binding (CPB) assays were developed. More recently, radioimmunoassay procedures have been developed which use both polyclonal and monoclonal antibodies.

In general, radioimmunoassay procedures in the art measure counts of radioactivity which are related to the affinity of the antibody for the hapten. Two parameters, $B_0$ and $B$, related to the counts of labeled hapten, are use in radioimmunoassay procedures. The $B_0$ value is the number of counts of labeled hapten bound under specific conditions by a given amount of antibody in the absence of unlabeled hapten. The B value is the number of counts of labeled hapten bound under the same conditions in the presence of unlabeled hapten. In a radioimmunoassay, radioactivity counts are conventionally presented as $B/B_0 \times 100$, referred to in the art as assay curve parameters, and are compared by plotting curve parameters against hapten concentration.

In order for antibodies to be suitable for use in a radioimmunoassay for $T_4$, the antibodies must have an affinity for $T_4$ which is neither too high nor too low. If the affinity of the antibody for $T_4$ is too low, the assay may not reach equilibrium between bound $T_4$ and unbound $T_4$, and any assay design may be invalid. If the affinity of the antibody for $T_4$ is too high, curve parameters, such as the 100, 90, 50, 10 and 0% ratios of $B/B_0$ may exhibit excessive deviations from the theoretical straight line plot. A radioimmunoassay for $T_4$ generally is configured so that the 50% $B/B_0$ ratio occurs within the accepted "normal" range of serum $T_4$ concentrations. In the absence of this configuration, determinations of serum $T_4$ concentrations above and below the normal range may be inaccurate.

Numerous monoclonal antibodies derived from mouse lymphocytes and mouse myeloma cells (mouse-mouse antibodies) have been produced and reported Representative disclosures are found in the following patents and published applications:

International Application No. PCT/US81/01291, publication number WO 82/01192 to Trowbridge, and U.S. Pat. Nos. 4,172,124, 4,349,528 and 4,196,265 to Koprowski.

Conventional polyclonal antisera have been used for many years for identifying antigens and haptens. In recent years monoclonal antibodies have been applied to such assays. European Patent Application No. 82302231, publication number 0064401, to Gillis discloses preparation of antibodies for use in serological detection of the T-cell activator interleukin-2. European Patent Application No. 81303286.9, publication number 0044722, to Kaplan et al discloses human-human monoclonal antibodies directed to a wide variety of haptens and antigens.

European patent application No. 81105024.4, publication number 44441, to Molinaro et al. describes mouse-mouse monoclonal antibodies specific to various haptenic drugs, such as gentimicin. Monoclonal antibodies to digoxin were described by Hunter in the J. of Immunology, 129,1165 (1982).

A monoclonal antibody kit for radioimmunoassay of serum $T_4$ levels is presently marketed by Mallinkrodt, Inc. Immunoassay Systems St. Louis, Mo. under the tradename SPAC$^R$ $T_4$. A monoclonal antibodies to $T_4$ are described by Wang et al., in two articles entitled "Monoclonal antibodies to Thyroid Hormones," *Monoclonal Antibodies and T-Cell Hybridomas*, p. 357, G. Hammerling et al., ed., Elsevier North Holland Biomedical Press Amsterdam Netherland 1981 and "Monoclonal Antibodies in Clinical Diagnosis," *Protides of the Biological Fluids*, p. 817, H. Peeters, ed., Pergamon Press, New York, N.Y. 1981. The antibodies described by Wang et al. are hereinafter referred to as Miles antibodies.

SUMMARY OF THE INVENTION

The method of the present invention for the immunoassay of $T_4$ uses a combination of particular monoclonal antibodies. In a preferred embodiment of the invention, the monoclonal antibodies are bound to a solid support. The monoclonal antibodies are produced by two new and separate hybridoma cell lines, identified as American Type Culture Collection (ATCC) Numbers HB 8499 and HB 8500. Each of the hybridomas was produced by inoculation of mice with $T_4$ conjugated to a carrier protein and fusion of the resulting lymphocytes with mouse myeloma cells. The use of the combination of monoclonal antibodies to $T_4$ provides an immunoassay for $T_4$ with improved affinity and accuracy.

The two monoclonal antibodies of this invention have different affinities for $T_4$ and can be used in the combination in any suitable proportion. When combined in suitable proportions, the two monoclonal antibodies of this invention achieve the desired curve parameters. The curve parameters may be chosen such that 50% $B/B_0$ ratio falls within the accepted "normal" range for serum $T_4$. The desired parameters may be attained with different batches of the monoclonal antibodies merely by variation of the proportion. By use of the antibody combination, the assay may be configured to operate in the range of maximum accuracy of radioimmunoassay design and thereby provide high sensitivity and accuracy over the range of $T_4$ concentrations encountered in a serum sample.

In the following detailed description of the invention, the following abbreviations are used:

ATCC—American Type Culture Collection
CGG—chicken gamma globulin
cpm—counts per minute
FBS—fetal bovine serum
FCA—Freund's complete adjuvant
FIA—Freund's incomplete adjuvant
HAT—hypoxanthine-aminopterin-thymidine
HT—hypoxanthine-thymidine
ID—intradermal
Ig—immunoglobulin
IP—intraperitoneal
IV—intravenous
LPRIA—liquid phase radioimmunoassay
MSID—multiple sites intradermal
PBS—phosphate buffered saline
PEG—polyethylene glycol
RIA—radioimmunoassay
RPMI—Roswell Park Memorial Institute medium
RT—room temperature
SC—subcutaneous
SPRIA—solid phase radioimmunoassay
TBG—thyroxine binding globulin
$T_4$—L-thyroxine
$T_4^*$—L-thyroxine $^{125}$I

DETAILED DESCRIPTION OF THE INVENTION

While this invention is satisfied by embodiments in many different forms, there will herein be described in detail a preferred embodiment of the invention, with the understanding that the present disclosure is to be considered as exemplary of the principles of the invention and is not intended to limit the invention to the embodiment described. The scope of the invention will be measured by the appended claims and their equivalents.

$T_4$ is a hapten, and as such it can interact with combining sites on a specific antibody. $T_4$ is non-immunogenic by itself, and thus does not cause the formation of antibodies when introduced into a host animal. However when $T_4$ is coupled to a carrier protein, it does elicit an immune response to produce antibodies capable of binding $T_4$. In the present invention, $T_4$ is chemically conjugated by conventional means to a carrier protein of molecular weight from about 5,000 to about 1,000,000 daltons, preferably from about 30,000 to about 200,000 daltons. Particularly useful carrier proteins to provide the conjugate are albumins or globulins, as for example CGG, although other classes of proteins, such as enzymes, may be used. Methods to attach such carrier materials to haptens are well known in the art and have been described by Parker in Radioimmunoassay of Biologically Active Compounds, Prentice-Hall, 1976.

For the production of monoclonal antibodies specific for $T_4$ in accordance with this invention, immunization is initiated by inoculation of a host animal with the conjugate. Although the preferred embodiment herein described utilizes a mouse as the host animal, it is understood that the invention is not limited to mouse-derived monoclonal antibodies and other species, as, for example, rat or human, may be used.

Particularly advantageous strains of mice for this invention are BALB/c mice and $C_3H$ mice. The mice may be from about 3 weeks to 30 weeks old at the time of the first inoculation, preferably 3 to 6 weeks old for the BALB/c mice and 25-30 weeks old for the $C_3H$ mice. Multiple inoculations are made over a period of from about 1 to about 300 days, preferably from about 1 to about 200 days. Inoculations may be made by the IP, IV or ID routes at one or more body sites with a dose of from about 5 to about 50 ug of conjugate per injection. The conjugate may be injected alone or may be mixed with a substance which increases the immunogenicity of the conjugate. Exemplary of such substances are, for example, a suspension of *B. pertussis*, or FCA or FIA. For injections made intravenously, the conjugate is dissolved in a physiologically acceptable vehicle, such as, for example, saline or PBS.

At the conclusion of the immunization period, the sensitized lymphocytes are harvested from various sites such as the lymph nodes or, preferably the spleen. The lymphocytes are suspended in a medium such as serum free RPMI 1640 medium (Seromed, Munchen, Federal Republic of Germany) at a concentration of about $5 \times 10^7$ cells/ml.

The isolated lymphocytes are fused with mouse myeloma cells whereby the ability of the lymphocytes to produce antibodies is joined with the ability of the myeloma cells to grow indefinitely in tissue culture In the selection of the myeloma cells to be used for the fusion, it is preferred that the myeloma cells and lymphocytes be derived from the same species to enhance the likelihood that the genetic and biochemical properties of the parent cells will be compatible and thus produce viable hybridomas. For the present invention, it is advantageous to select a myeloma line which does not produce antibodies itself, i.e., a non-producing cell line, so that the resulting hybridoma will only produce antibodies specific for $T_4$. In addition, it is advantageous to select a myeloma cell line in which a deficiency of an enzyme essential for nucleotide synthesis has been introduced by pretreatment with a cytotoxic agent, to thereby facilitate subsequent separation of hybridoma cells from unfused lymphocytes and myeloma cells. Preferred enzyme deficient myeloma cell lines are those which cannot grow in the culture medium conventionally known as HAT medium as described in Science 145,709 (1964). A particularly preferable myeloma cell line for the present invention is the non-antibody-producing P3X63-Ag8.653 (ATCC CRL 1580), described by Kearney, et al., J. of Immunology, 123, 1548 (1979). It is understood, however, that other tumor cell lines may be used, as, for example, P3/NS1/1-Ag4-1 (ATCC TIB 18). These and other mouse myeloma cell lines have been characterized and are on deposit with the ATCC.

In preparation for fusion, the myeloma cells are selected at mid-log growth phase. The cells are counted, isolated from their stock medium by centrifugation, and the pellet is suspended in serum free RPMI at a concentration of about $5 \times 10^6$ cells/ml Fusion usually occurs at a rate of about 1 hybridoma per $1 \times 10^5$ parent lymphocyte cells used. In order to get sufficient hybridomas for subsequent processing, it is advantageous to use from about $1 \times 10^6$ to $1 \times 10^{10}$ preferably about $1 \times 10^7$ to about $1 \times 10^8$ lymphocytes for the fusion. Any ratio of lymphocytes to myeloma cells may be used, but a higher percentage of fusion events takes place if a ratio of lymphocytes to myeloma cells of from about 5:1 to about 20:1, preferably about 8:1 to 12:1 is used. Thus, preferably, about $1 \times 10^7$ myeloma cells are used for fusion with about $1 \times 10^8$ lymphocytes. A conventional fusing agent is used, as, for example, sendai virus or, preferably, PEG. The PEG may be of any molecular weight from about 1000 to about 6000, preferably about 3500 to 4500. It is used as a solution of from about 25% to about 50% in RPMI medium, preferably a concentration of about 35% to about 40% is used.

Fusion is carried out by mixing the fusion agent with the desired cell quantities and ratio. The quantity of fusing agent solution used is about 20-40% of the total volume of the fusion mixture, preferably about 25%. A particularly preferable fusion mixture is about 0.5 ml of 37.5% PEG 6000 in RPMI added to a cell pellet containing $5 \times 10^7$ lymphocytes and $5 \times 10^6$ myelomas. The mixture is maintained at room temperature for from about 5 to about 20, preferably about 10 minutes.

The hybridomas are separated from unfused myeloma and lymphocyte cells by addition of the fusion mixture to a medium which will support growth of the hybridomas but not the unfused cells. Conventional HAT concentration as defined in Science 145, 709 (1964) in the presence of RPMI and FBS may be used for this purpose. Preferably a mixture of 4 ml RPMI and 1 ml FBS containing the defined HAT concentration is used. Aliquots of the mixture are added to a multiplicity of wells of a microtiter plate. After an appropriate incubation period, usually about 2 weeks, some of the wells will show growth by macroscopic observation. However, since a mixed lymphocyte population was presented to the myeloma cells for fusion, the resulting hybridomas will secrete antibodies of differing specificities to $T_4$.

Conventional assay means, as, for example, SPRIA and LPRIA, are used to determine these specificities. In a typical procedure, polyvinyl chloride microtiter plates are coated with anti-mouse Ig and incubated with culture supernatants from wells showing hybridoma growth. Incubation with known amounts of $T_4^*$ is also carried out, and the amount of bound $T_4^*$ is determined using a gamma counter. The amount of radioactivity is proportional to the amount of antibody specific for $T_4$ in the supernatant.

The sensitivity, affinity and cross-reactivity of the monoclonal antibodies to $T_4$ may be determined using conventional LPRIA. Further specificity determination may be made using a competitive LPRIA using triiodothyronine ($T_3$). The hybridoma cells in those wells thus determined to contain antibodies of sufficient specificity and affinity for $T_4$ are cloned by conventional limiting dilution procedures to ensure monoclonality. This procedure is repeated at least 3 times to confirm stability of the hybridoma cell lines. From the final limiting dilution clone plate indicating stability of the hybridoma, one hybridoma clone is isolated from each individual hybridoma cell line and expanded to about $2 \times 10^8$ cells per ml. Seed stocks of this hybridoma are frozen and stored in ampoules, preferably at less than $-100°$ C, under nitrogen, at about $1 \times 10^7$ cells per ml. Stability is evaluated after freezing by further cloning at limiting dilution.

For production of monoclonal antibodies from the selected hybridoma, growth may be carried out in vitro according to known tissue culture techniques, such as is described by Cotton et al. in European Journal of Immunology, 3, 136 (1973), or preferably the hybridoma may be grown in vivo as tumors in a histocompatible animal. In this preferred embodiment, a seed ampoule is thawed, and the hybridoma cells are expanded and injected into, for example, syngeneic mice at $1 \times 10^6$ cells/per animal. In a particularly preferred embodiment, the mice are primed with a substance as, for example, pristane (2,6,10, 14 tetramethyl pentadecane) one week before injection to increase the formation of ascites fluid. After a time period of from about one to three weeks, tumor bearing animals are tapped for ascites fluid. Further testing of the monoclonal antibodies thus prepared for specificity to $T_4$ is carried out by RIA as described above.

The hybridomas of the present invention, obtained by immunization of BALB/c mice and C3H mice are designed ATCC HB 8499 and ATCC HB 8500, respectively, and have been deposited with the American Type Culture Collection. The monoclonal antibodies elaborated by the hybridoma designated ACCC HB 8499 and by the hybridoma designated ATCC HB 8500 are homogeneous and react with concentrations of $T_4$ as low as 1.8 ng/ml. They have high specificity for $T_4$ and show cross reactivity to $T_3$ which may be as low as 0.12%. The monoclonal antibody from the hybridoma designated ATCC HB 8500 has greater affinity for $T_4$ than any known $T_4$ specific monoclonal antibody. This affinity may be as high as $2.6 \times 10^9$ liters per mole.

The monoclonal antibodies of the invention are useful in providing improved means for immunoassay of $T_4$. Any immunoassay technique may be used, as, for example, competitive immunoassay, inhibition immunoassay, or sandwich immunoassay. In a preferred embodiment of the invention, the immunoassay is a solid phase immunoassay. Any suitable solid phase may be used, preferably a polymeric substrate such as polypropylene, polyvinyl chloride, polystyrene, polyethylene, latex or polyacrylamide. When combined on a suitable solid support, their affinities for $T_4$ make these monoclonal antibodies particularly advantageous for use in an improved SPRIA for $T_4$. The assay is very accurate over the range of serum $T_4$ concentrations encountered in clinical samples.

The monoclonal antibody from the hybridoma designated ATCC HB 8499 may be used in the assay from 0.0025% to 0.05%, preferably from 0.013% to 0.025%. The monclonal antibody from the hybridoma designated ATCC HB 8500 may be used in the assay from 0.005% to 0.025%, preferably from 0.0067% to 0.0083%.

The present invention will be illustrated by the following examples, but is not intended to be limited thereby.

EXAMPLE 1

Preparation of $T_4$ - CGG Conjugate:

$T_4$ (116.5 mg, 150 uM) was placed in 5 ml of 0.1 m phosphate buffer, pH 11.9. Eighty five ul of toluene diisocyanate (TDIC) was added and the mixture was stirred vigorously at 0° C for 30 minutes, centrifuged at 0° C, and the supernatant allowed to incubate for 1 hour at 0° C and added to a solution of 70 mg of CGG, MW 170,000 in 5 ml of 0.1 M phosphate buffer, pH 11.9. After 1 hour at 37° C the mixture became cloudy. The mixture was dialyzed against 0.1 M $(NH_4)_2CO_3$ solution overnight to destroy any excess TDIC, and then dialyzed against 0.1 M phosphate buffer, pH 11.9. The solution thus prepared was used for inoculation.

Immunization BALB/C mice which were 5 weeks old on day 1 were immunized according to the following protocol:

| DAY | INJECTANT | QUANTITY (ug) of $T_4$—CGG | ROUTE |
|---|---|---|---|
| 1 | T4-CGG 1:1 CFA* | 50 | IP |
| 33 | T4-CGG 1:1 FIA | 10 | IP |
| 49 | T4-CGG 1:1 F1A | 10 | IP |
| 110 | T4-CGG 1:1 F1A | 10 | IP |
| 140 | T4-CGG 3:1 FIA | 10 | IP |
| 168 | T4-CGG 1:1 FIA | 10 | IP |
| 207 | T4-CGG in PBS | 10 | IV |
| 208 | T4-CGG in PBS | 10 | IV |
| 209 | T4-CGG in PBS | 10 | IV |
| 210 | Spleens harvested for fusion | | |

*A mixture of equal parts by volume.

C3H mice 27 weeks old on day 1 were immunized by MSID injection with 10 ug of T4-CGG and 50 ul of B. pertussis suspension on days 1, 14, 33, 49, 63, 77 and 100. On day 245, a solution of 10 ug of T4-CGG in saline was injected IP. On day 248, the spleens were harvested for fusion.

Isolation of Spleen Cells

The mice from each group were sacrificed by cervical dislocation and the spleens were removed into a 60 mm. petri dish containing 5 ml of sterile RPMI containing 5% FBS. After rinsing, the spleens were transferred to a second dish and perfused. The spleen sacks were teased apart and the cells were pipetted into a 15 ml centrifuge tube. Centrifugation was carried out at 500 rpm for 5 min. The pellet was suspended in serum free RPMI to yield $5 \times 10^7$ lymphocytes/ml.

Preparation of P3X68-Ag8.653 Myeloma Cells

Myeloma cells at the midpoint of the log growth phase were counted, centrifuged at 500 rpm for 5 min. and suspended in serum free RPMI at room temperature to give a suspension of $5 \times 10^6$ cells/ml.

Fusion

One ml each of spleen and myeloma cells was mixed in a 17 x 100 mm round bottom tube and topped with about 10 ml of serum free RPMI at RT. The supernatant was decanted, the tube was tapped to break up the pellet, and 0.5 ml of 37.5% PEG in RPMI previously incubated under 7% $CO_2$ was added. The tube was tapped to mix and incubated at RT for 10 min., during which a 3 minute spin at 500 rpm was carried out.

Serum free RPMI (4 ml) was added to quench the reaction and the tube was tapped to mix and poured into a mixture of 5 ml RPMI —20% FBS, 1 ml FBS and 0.1 ml of modified HAT. Incubation overnight at 37° C was then carried out.

Growth and Selection

On day 1 after fusion, 23.5 ml of RPMI-20% FBS-HAT medium were added so that the concentration of spleen cells was $2 \times 10^7/14$ ml. Using a sterile 10 ml glass pipet, 2 drops of the mixture were added to each well of a 96-well microtiter plate. On day 9, 1 drop of RPMI-20% FBS-HT medium was added to each well. When growth appeared macroscopically (about day 14), the supernatants were taken for testing and replaced with RPMI-20% FBS-HT medium.

Screening of Supernatants for Antibodies

The supernatant from wells showing growth were tested by solid phase RIA for antibodies to $T_4$. Ninety six well polyvinyl chloride microtiter plates (Dynatech Labs) were charged with 100 ul of antimouse IgG diluted in pH 9.6 carbonate buffer, leaving several wells for positive and negative controls. The negative control for this assay was P3X63-Ag8.653 supernatant diluted 1:5 with PBS-0.05% Tween 20 (polyoxyethylenesorbitan monolaurate). Positive control was a 1:300 dilution of Miles antibodies, diluted in PBS-0.05% Tween 20 or a 1:5 dilution of an established $T_4$ hybridoma that is available either as fresh or frozen supernatant. The microtiter plate was covered with Parafilm and incubated overnight at 4° C. The plate was emptied and the wells were washed 3 times with PBS-0.05% Tween 20. Samples and appropriate negative and positive controls were diluted 1:5 with PBS —0.05% Tween 20 and 50 ul dispensed per well to the washed plate. The plate was covered with parafilm, incubated 1 hour at 37° C, and washed 3 times with PBS-0.05% Tween 20. $T_4^*$ was diluted with PBS-0.05% Tween 20 to obtain approximately 70,000 cpm per 50 ul, and 50 ul was dispensed to each well and to duplicate $12 \times 75$ mm polypropylene tubes labeled "total cpm." The plates were covered with Parafilm, incubated 1 hour at 37° C, aspirated to remove the label, and the wells were washed 3 times with PBS-0.05% Tween 20. After drying the plates on a paper towel, the radioactivity was counted in the gamma counter for 30 seconds per sample. The radioactivity in the "total cpm" tubes was also counted.

Stability Test of Selected Clones

The cultures of those hybridomas shown by SPRIA and LPRIA to produce antibodies specific to $T_4$ were counted by staining with Trypan Blue and diluted to about 10 viable cells/ ml. About 100 ul of cell suspension were added per well to a 96 well plate (calculated to provide about 1 cell per well), and the plate was incubated under 7% $CO_2$. About day 14, visible hybridomas were tested for antibody production. The screening and stability test steps were repeated several times with the $T_4$ specific antibody-producing hybridomas showing the highest stability and antibody specificity. A final selection of the best hybridoma from each mouse line was made and the hybridomas designated as follows:
from BALB/c mice—ATCC HB 8499
from $C_3H$—mice ATCC HB 8500

What is claimed is:

1. A monoclonal antibody produced by a hybridoma cell line formed by fusion of cells from a mouse myeloma cell line with lymphocytes isolated from a mouse strain which has previously been immunized with L-thyroxine conjugated to a protein carrier, which monoclonal antibody:
   reacts with L-thyroxine in an aqueous-based fluid when said L-thyroxine is present in said fluid at a concentration of 1.8 ng/ml to about 20 ng/ml
   has an affinity for said L-thyroxine of no less than $2.6 \times 10^9$ liters per mole and has a cross reactivity to triiodothyronine of no greater than 0.12%.

2. A monoclonal antibody in accordance with claim 1 wherein said mouse myeloma cell line is the cell line identified as $P3 \times 63$ - Ag 8.653.

3. A monoclonal antibody in accordance with claim 1 wherein said mouse strain is selected from the group of strains consisting of BALB-c and $C_3H$ strains.

4. A combination of monoclonal antibodies useful in an immunoassay for thyroxine comprising a monoclonal antibody produced by the hybridoma designated ATCC HB 8499 and a monoclonal antibody produced by the hybridoma designated ATCC HB 8500.

5. A monoclonal antibody in accordance with claim 1 produced by a hybridoma cell line designated AATCC HB 8499.

6. A monoclonal antibody in accordance with claim 1 produced by a hybridoma cell line designated ATCC HB 8500.

7. A hybridoma cell line designated ATCC HB 8499.

8. A hybridoma cell line designated ATCC HB 8500.

* * * * *